US011511256B2

(12) United States Patent
Liu et al.

(10) Patent No.: US 11,511,256 B2
(45) Date of Patent: Nov. 29, 2022

(54) FLEXIBLE PRODUCTION OF GASOLINE AND JET FUEL IN ALKYLATION REACTOR

(71) Applicant: LUMMUS TECHNOLOGY LLC, Bloomfield, NJ (US)

(72) Inventors: Zan Liu, Houston, TX (US); Jackeline Medina Bolívar, Houston, TX (US); Maurice Korpelshoek, Houston, TX (US); Romain Lemoine, Houston, TX (US); Manoj Som, Houston, TX (US)

(73) Assignee: LUMMUS TECHNOLOGY LLC, Bloomfield, NJ (US)

( * ) Notice: Subject to any disclaimer, the term of this patent is extended or adjusted under 35 U.S.C. 154(b) by 0 days.

(21) Appl. No.: 16/881,734

(22) Filed: May 22, 2020

(65) Prior Publication Data

US 2020/0368709 A1 Nov. 26, 2020

Related U.S. Application Data

(60) Provisional application No. 62/852,744, filed on May 24, 2019.

(51) Int. Cl.
  *C07C 2/62* (2006.01)
  *C07C 7/00* (2006.01)
  *B01J 19/00* (2006.01)
  *C10L 1/06* (2006.01)

(52) U.S. Cl.
  CPC ......... *B01J 19/004* (2013.01); *B01J 19/0013* (2013.01); *C07C 2/62* (2013.01); *C07C 7/005* (2013.01); *C10L 1/06* (2013.01); *B01J 2219/00051* (2013.01); *B01J 2219/00164* (2013.01); *C10L 2200/043* (2013.01); *C10L 2200/0423* (2013.01); *C10L 2270/023* (2013.01); *C10L 2270/04* (2013.01)

(58) Field of Classification Search
  None
  See application file for complete search history.

(56) References Cited

U.S. PATENT DOCUMENTS 2,264,447 A * 12/1941 Meier ................. C07C 7/14883
                                                   585/719
3,657,377 A    4/1972 Kemp
4,658,073 A *  4/1987 Tabak ....................... C07C 2/12
                                                   585/314
5,648,586 A *  7/1997 Sampath .................. C07C 2/62
                                                   585/300
6,774,275 B2   8/2004 Smith, Jr. et al.
(Continued)

FOREIGN PATENT DOCUMENTS

CN    102099443 B    11/2012
CN    103361121 A    10/2013

OTHER PUBLICATIONS

International Search Report issued in corresponding International Application No. PCT/US2020/034265, dated Sep. 4, 2020 (4 pages).
(Continued)

*Primary Examiner* — Philip Y Louie
(74) *Attorney, Agent, or Firm* — Osha Bergman Watanabe & Burton LLP

(57) ABSTRACT

Systems and processes for the flexible production of gasoline and jet fuel via alkylation of C4 and C5 olefins.

5 Claims, 9 Drawing Sheets

(56) References Cited

U.S. PATENT DOCUMENTS

| | | | |
|---|---|---|---|
| 6,858,770 B2* | 2/2005 | Smith, Jr. | C07C 2/62 |
| | | | 585/720 |
| 2009/0306448 A1 | 12/2009 | Smith, Jr. et al. | |
| 2012/0264994 A1 | 10/2012 | Hurst et al. | |
| 2013/0066130 A1 | 3/2013 | Luo et al. | |
| 2018/0158377 A1 | 6/2018 | Ikarashi et al. | |

OTHER PUBLICATIONS

Written Opinion issued in corresponding International Application No. PCT/US2020/034265, dated Sep. 4, 2020 (8 pages).

* cited by examiner

FLEXIBLE PRODUCTION OF GASOLINE AND JET FUEL IN ALKYLATION REACTOR

FIELD OF THE DISCLOSURE

Embodiments disclosed herein relate generally to alkylation of olefins with isoparaffins in the presence of sulfuric acid catalysts. More particularly, embodiments herein relate to a flexible alkylation system and operation scheme to maximize either gasoline, jet fuel or solvent production.

BACKGROUND

Isoparaffin-olefin alkylation processes are a key route to the production of highly branched hydrocarbons with high octane numbers. Alkylation is accomplished by reacting isoparaffins (for example, isobutane or isopentane) with olefins in the presence of an acid catalyst, such as hydrogen fluoride, sulfuric acid, ionic liquid or solid acidic catalyst. The alkylation product has been adopted as a premium blending component in the gasoline pool, as it has low sulfur, olefin and aromatic content. However, with increasing demand for jet fuel relative to gasoline, it becomes economical to repurpose the alkylation unit for jet fuel production.

The alkylation process involves complex reaction chemistry. It contains major reactions steps including olefin activation, olefin addition, hydride transfer, polymerization/oligomerization, hydrogen transfer, cracking and isomerization. The complex reaction chemistry contributes to a wide distribution of carbon numbers of product. The typical alkylation product has carbons numbers from C5 to C14. The carbon number distribution of gasoline and jet fuel has an overlap in the range of C9 to C14. The alkylation process thus has the potential to coproduce gasoline and jet fuel.

SUMMARY OF THE CLAIMED EMBODIMENTS

Systems and processes for isoparaffin-olefin alkylation have now been developed to flexibly vary the ratio of gasoline to jet fuel produced.

In one aspect, embodiments disclosed herein relate to systems for flexible production of gasoline and jet fuel. The systems may include an alkylation reaction zone including one or more reactors for reacting C4 olefins, C5 olefins, C6 olefins, C4-C5 olefins, or C4-C6 olefins with C4-C6 isoparaffins in the presence of sulfuric acid alkylation catalyst to produce a hydrocarbon effluent and a spent acid stream. A flow line may provide C4 olefins to the alkylation reaction zone. A flow line may also provide C5 olefins to the alkylation reaction zone. Yet another flow line may provide fresh acid alkylation catalyst to the alkylation reaction zone. A deisobutanizer may be provided for separating the hydrocarbon effluent into an isobutane fraction, a n-butane fraction, and a C5+ fraction. A deisopentanizer may be provided for separating the C5+ fraction into an isopentane fraction and a C6+ fraction. Further, a splitter may be provided for separating the C6+ fraction into a light alkylate overhead fraction and a heavy alkylate bottoms fraction. Flexibility in the product mixture from the alkylation reaction zone may be provided via: (i) a flow system for recycling the isobutane fraction to the alkylation reaction zone, recovering the isobutane fraction as an isobutane product, and both recycling a portion of the isobutane fraction to the alkylation reaction zone and recovering a portion of the isobutane fraction as an isobutane product; (ii) a flow system for recycling the isopentane fraction to the alkylation reaction zone, recovering the isopentane fraction as an isopentane product, and both recycling a portion of the isopentane fraction to the alkylation reaction zone and recovering a portion of the isopentane fraction as an isopentane product; and (iii) a flow system for recycling the light alkylate fraction to the alkylation reaction zone, recovering the light alkylate as a light alkylate product, and both recycling a portion of the light alkylate fraction to the alkylation reaction zone and recovering a portion of the light alkylate fraction as a light alkylate product. In some embodiments, the system may further include a flow line for providing C6 olefins to the alkylation reaction zone.

In another aspect, embodiments herein relate to systems for flexible production of gasoline and jet fuel. The systems may include an alkylation reaction zone comprising one or more reactors for reacting C4 olefins, C5 olefins, C6 olefins, C4-C5 olefins, or C4-C6 olefins with isoparaffins in the presence of sulfuric acid alkylation catalyst to produce a hydrocarbon effluent and a spent acid stream. A flow line may provide C4 olefins to the alkylation reaction zone. A flow line may also provide C5 olefins to the alkylation reaction zone. Yet another flow line may provide fresh acid alkylation catalyst to the alkylation reaction zone. A deisobutanizer may be provided for separating the hydrocarbon effluent into an isobutane fraction, a n-butane fraction, and a C5+ fraction. A deisopentanizer may be provided for separating the C5+ fraction into an isopentane fraction and a C6+ fraction. Further, a splitter may be provided for separating the C6+ fraction into a light alkylate overhead fraction and a heavy alkylate bottoms fraction. Flexibility in producing gasoline or jet fuel in the alkylation reaction zone may be provided by: (i) a flow system for recycling the isobutane fraction to the alkylation reaction zone, recovering the isobutane fraction as an isobutane product, and both recycling a portion of the isobutane fraction to the alkylation reaction zone and recovering a portion of the isobutane fraction as an isobutane product; (ii) a flow system for recycling the isopentane fraction to the alkylation reaction zone, recovering the isopentane fraction as an isopentane product, and both recycling a portion of the isopentane fraction to the alkylation reaction zone and recovering a portion of the isopentane fraction as an isopentane product; and (iii) a control system configured to adjust a flow rate of each of the C4 olefins, C5 olefins, the recycle isobutane fraction, and the isopentane recycle fraction to the alkylation reaction zone to selectively increase or decrease a ratio of gasoline to jet fuel range hydrocarbons produced in the alkylation reaction zone.

In another aspect, embodiments herein relate to processes for flexible production of gasoline and jet fuel. The processes may include feeding isoparaffins and olefins, including C4 and/or C5 olefins, for example, to an alkylation reaction zone including one or more reactors for reacting the C4-C5 olefins with the isoparaffins in the presence of sulfuric acid alkylation catalyst to produce a hydrocarbon effluent and a spent acid stream. The hydrocarbon effluent may be separated into an isobutane fraction, a n-butane fraction, and a C5+ fraction, and the C5+ fraction may be further separated into an isopentane fraction and a C6+ fraction. The C6+ fraction may be separated into a light alkylate overhead fraction and a heavy alkylate bottoms fraction. The process may also include alternately: increasing a ratio of gasoline to jet fuel range hydrocarbons in the alkylate; and decreasing a ratio of gasoline to jet fuel range hydrocarbons in the alkylate.

The alternately increasing and decreasing, in some embodiments, may include adjusting a flow rate to the alkylation reaction zone of each of the C4 olefins, the C5 olefins, an isobutane recycle fraction, an isopentane recycle fraction, and a light alkylate recycle fraction. The alternately increasing and decreasing may additionally or alternatively include adjusting a reaction temperature of one or more of the one or more reactors in the alkylation reaction zone to increase or decrease a ratio of gasoline to jet fuel range hydrocarbons produced in the alkylation reaction zone. In other embodiments, the alternately increasing and decreasing may additionally or alternatively include adjusting a flow rate of fresh acid catalyst to the one or more reactors in the alkylation reaction zone to increase or decrease a ratio of gasoline to jet fuel range hydrocarbons produced in the alkylation reaction zone. In yet other embodiments, the alternately increasing and decreasing may additionally or alternatively include adjusting operating conditions in the one or more reactors in the alkylation reaction zone to increase or decrease a ratio of gasoline to jet fuel range hydrocarbons produced in the alkylation reaction zone. In still further embodiments, the alternately increasing may include recovering the C5+ fraction as a gasoline product fraction.

By properly changing the feedstock, composition of recycle isobutane and isopentane, and varying operating conditions, the reaction pathways can be controlled to either maximize hydride transfer (alkylation) or maximize olefin polymerization, oligomerization, and/or cracking. Systems and processes herein provide this flexibility, allowing an operator to tune the alkylation process to maximize gasoline, maximize jet fuel, or co-produce these at intermediate ratios so as to meet market demand and/or to maximize revenue.

Other aspects and advantages will be apparent from the following description and the appended claims.

DETAILED DESCRIPTION

Embodiments herein relate to flexible production of gasoline and jet fuel via isoparaffin-olefin alkylation. The alkylation reaction may be conducted in an alkylation reaction zone, which may include one or more alkylation reactors. The alkylation reactor(s) may be any type of reactor which facilitates alkylation using a liquid acid alkylation catalyst, such as HF or sulfuric acid. The alkylation reactor(s) may be vertical or horizontal, and may have a static or non-static mixing device. When the alkylation reactor system includes multiple reactors, the hydrocarbon flow may be in parallel or in series, and the acid catalysts may be injected into the reactors in parallel or in series.

Systems useful in flexibly producing gasoline and jet fuel may also include separators, including a deisobutanizer, a deisopentanizer and an alkylate splitter. The purpose of deisobutanizer is to separate isobutane, n-butane and C4+ hydrocarbons. The deisopentanizer is used to separate isopentane from C5+ hydrocarbons; depending on the operation mode (gasoline, jet fuel or co-production modes), isopentane may be recycled back to the alkylation reaction zone. The splitter is used to separate the whole alkylate into light alkylate, which can be used or processed into solvent, motor gasoline blending stock or aviation gasoline blending stock. The heavy alkylate can be used as blending component for the jet fuel pool. Depending on the operation mode, some of the light alkylate or the isohexane contained therein may be recycled back to the alkylation reaction zone.

Figure 1:
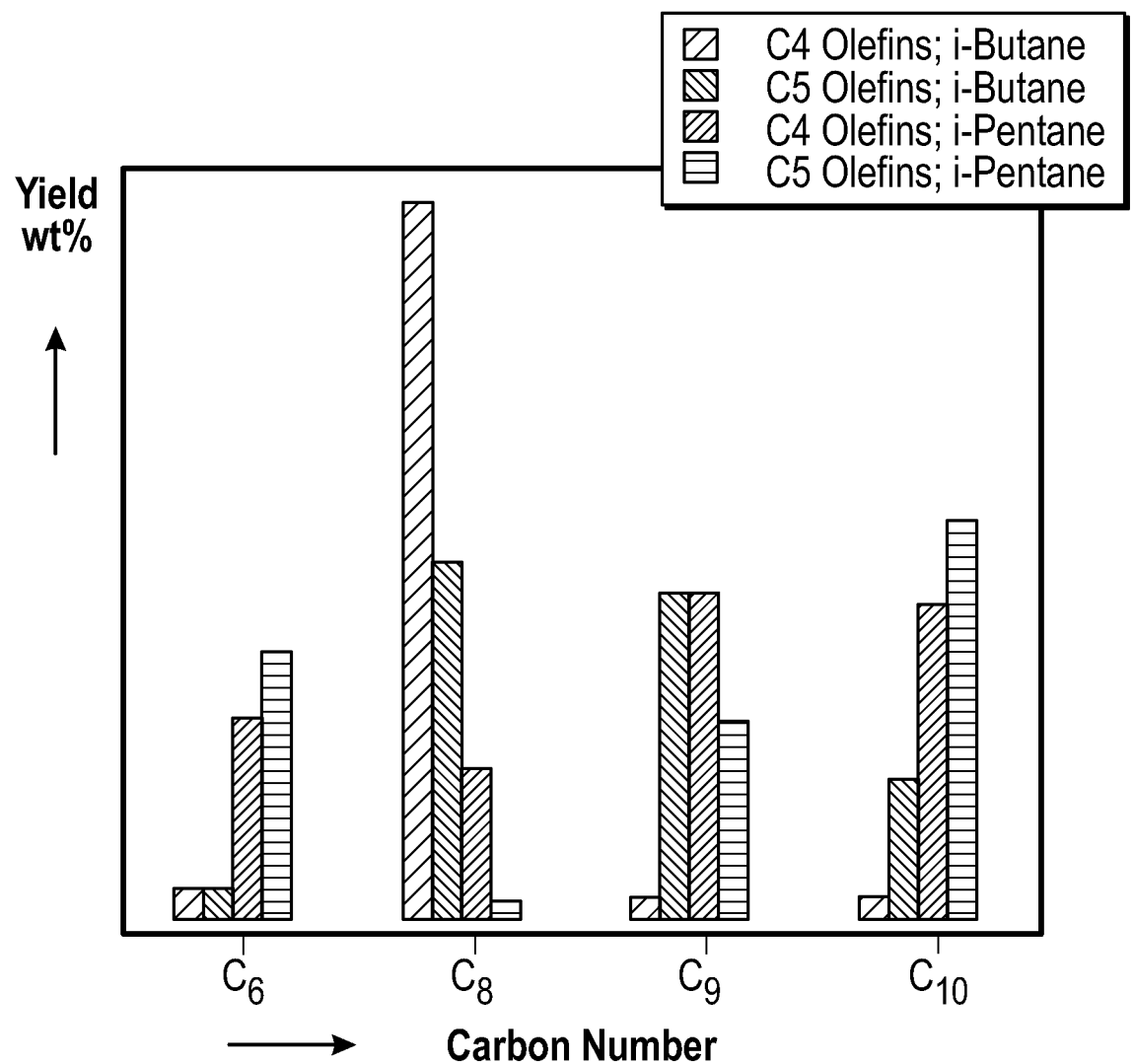
FIG. 1 is a chart illustrating the effect of olefin type and isoparaffin type on the product distribution according to embodiments disclosed herein.

Systems herein may utilize up to three ways to adjust the relative production of gasoline and jet fuel. The first way systems and processes herein control the ratio of gasoline to jet fuel is to adjust the olefin type. As shown in FIG. 1, for a given iso-paraffin, alkylation of C4 olefins with either isobutene or isopentane tends to generate more C8 product than C5 olefins. Alkylation of C5 olefins with either isobutene or isopentane results in a higher product yield in the jet fuel range.

The second way systems and processes herein control the ratio of gasoline to jet fuel is to adjust the type of iso-paraffin. As shown in FIG. 1, with a given olefin type, the employment of isopentane tends to generate heavier hydrocarbons compared to alkylation using isobutane. Thus, a very effective way to adjust the production of gasoline and jet fuel is to control the recycle isobutane and isopentane by adjusting the operation of the deisobutanizer and deisopentanizer. In a maximum gasoline production mode, the recycle of isobutane may be maximized, and the isopentane may be removed as a net product. In this case, the hydrogen transfer reaction is enhanced, leading to more isopentane production, and higher content of C8. In contrast, in a maximum jet fuel production mode, isobutane may be removed as a net product while recycling as much isopentane as possible, as the higher concentration of isopentane will suppress the hydrogen transfer reaction, leading to production of more C9+ hydrocarbons. In addition, the recycle of isohexane may also increase the production of heavier hydrocarbons, leading to a higher yield of jet fuel.

Figure 2:
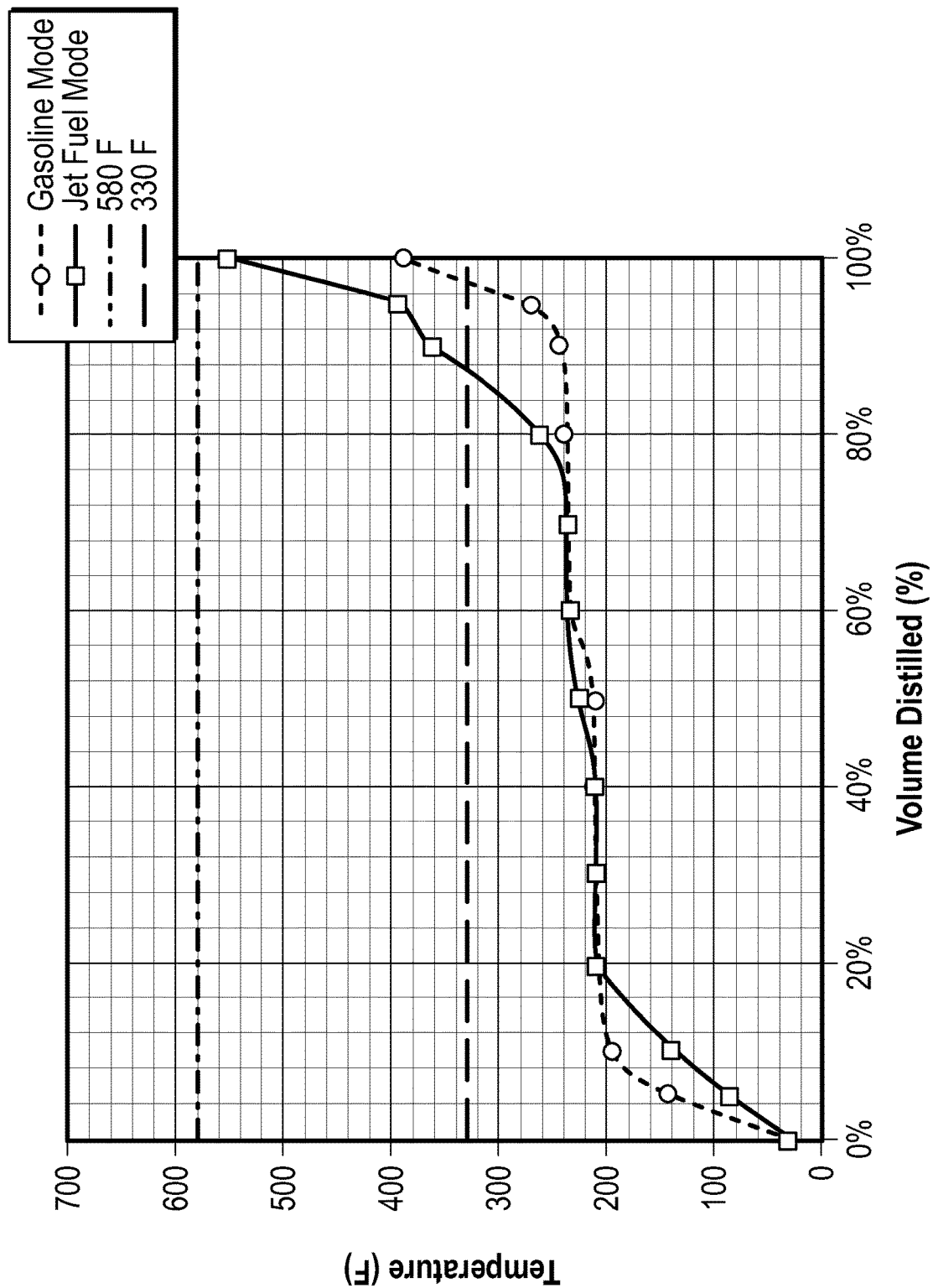
FIG. 2 is a graph illustrating a shift in jet fuel production according to embodiments of the flexible alkylation processes and systems disclosed herein.

The third way systems and processes herein control the ratio of gasoline to jet fuel is to adjust the operating conditions, including acid strength (in the case of liquid acid alkylation), temperature, space velocity, recycle isobutane/olefin ratio, and mixing intensity. With a given olefin and isoparaffin type, lower acid strength, higher temperature, higher space velocity, lower Isoparaffin/Olefin (I/O) ratio, and lower mixing intensity will lead to more C9+ production, thus maximizing jet fuel production. As shown in FIG. 2, by varying the operating conditions according to embodiments herein, the production of hydrocarbons in the jet fuel range (330-580° F./165-305° C.) may be increased significantly.

Figure 3:
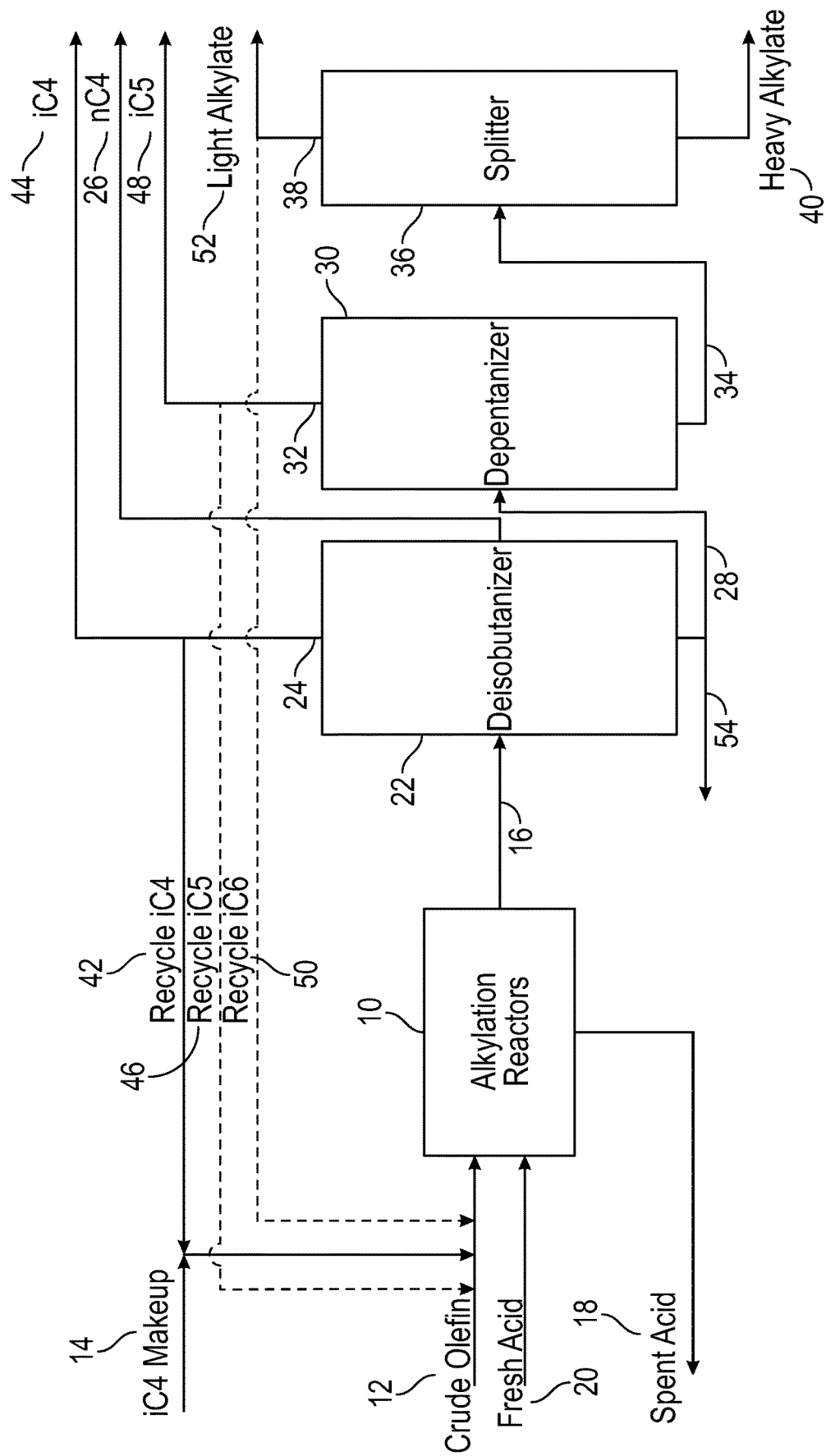
FIGS. 3-6 illustrate simplified process flow diagrams of systems according to embodiments herein.

As described above, systems and processes herein may flexibly adjust or optimize gasoline and jet fuel production via alkylation. A simplified process flow diagram of an alkylation system according to embodiments herein is illustrated in FIG. 3. As illustrated in FIG. 3, a system for flexible production of gasoline and jet fuel according to embodiments herein may include an alkylation reaction zone 10 including one or more alkylation reactors, and when two or more are used, the reactors may be in series and/or in parallel. The alkylation reactor(s) may be used for reacting C4-C5 olefins with isoparaffins in the presence of an acid alkylation catalyst to produce a hydrocarbon effluent and a spent acid stream. In various embodiments, C4 olefins, C5 olefins, and/or C6 olefins may be provided to the alkylation reaction zone.

The C4-C6 olefins may be provided as one or more crude olefin streams 12, including a C4 olefin stream, a C5 olefin stream, or a mixed C4/C5 olefin stream, for example. The crude C4 and C5 olefin streams may include mixtures of olefins and paraffins. The olefins contained therein may include n-olefins, iso-olefins, or mixtures thereof. Paraffins may include, for example, C4 alkanes (n-butane, isobutane), C5 alkanes (n-pentane, neopentane, and isopentane), or mixtures thereof. In some embodiments, high purity isoparaffins, such as an isobutane or an isopentane feed 14 may alternatively or additionally be provided. In other embodiments, the olefins and the isoparraffins may be provided separately. In some embodiments, a C4 olefin-containing feedstock may have greater than 50 wt % C4 olefins. In some embodiments, a C5 olefin-containing feedstock may have greater than 50 wt % C5 olefins.

The alkylation reaction may be catalyzed with sulfuric acid or HF, for example. Sulfuric acid may be used, for example, at a concentration in excess of 80 weight percent in some embodiments, in excess of 88 percent in other embodiments, and in excess of 96 percent in yet other embodiments. The alkylation process includes reacting isoparaffins with olefins in the presence of the acid catalyst in the one or more reactors of the alkylation reaction zone 10. The reaction products are then separated in the alkylation reaction zone to recover a hydrocarbon-rich phase and an acid-rich phase. The hydrocarbon-rich phase may be further treated in the alkylation reaction zone to remove sulfate esters from the hydrocarbon phase, if necessary, among other operations, to produce a hydrocarbon effluent 16 which may include unreacted isoparaffin and alkylate products.

A portion of the acid-rich phase may be recycled to the same alkylation reactor, such as to maintain a desired acid concentration in the reactor. The remaining acid may be recovered as a spent acid fraction, which may be forwarded to a different reactor (acid cascading) in the alkylation reaction zone or may be recovered via flow line 18 for spent acid recovery. A fresh acid feed 20 may also be provided to maintain the reactors at a desired acid concentration. For example, sulfuric acid fed to the alkylation reaction zone may include fresh and/or recycled sulfuric acid. In some embodiments, the concentration of sulfuric acid phase entering the alkylation reactors may be maintained at a concentration that titrates as below 99.8 weight percent strength sulfuric acid/water mixtures or less. In other embodiments, the sulfuric acid may be maintained at a concentration range titrating as 20 to 96 weight percent sulfuric acid/water mixtures; titrating as 25 to 75 weight percent sulfuric acid/water mixtures in other embodiments; and titrating as 30 to 70 weight percent sulfuric acid/water mixtures in yet other embodiments. It can be noted that that the acid phase in these instances is composed of sulfuric acid, sulfate esters, ASO (acid soluble oils) and water. The acid phase does not contain significant quantities of water, typically 0-5% by weight, and for the purposes of describing the acid content, the terminology "titrates as" or "titrating as" is used to indicate a sulfuric acid/water mixture which has the same acidity, understanding that the acid mixture used herein is more complex in chemical makeup. Measurement of the acidity may be measured, for example, using a METTLER DL-77 or a METTLER T-90 titrator.

Thus, in various embodiments, fresh acid may be fed in addition to the spent acid or recycle acid fed to the alkylation reactors in the alkylation reaction zone. The flowrates of the fresh acid streams, the portion of the recovered acid recycled to the alkylation reactor and the portion of the spent acid forwarded to another alkylation zone or to acid recovery may be controlled in order to achieve a desired or optimal acid strength in each respective alkylation reactor. In some embodiments, the alkylation reaction zone may include a C4 alkylation reactor and a C5 alkylation reactor, for example. Acid recycle, fresh acid, and acid cascading may be controlled such that the sulfuric acid in a C4 alkylation reactor may be maintained at a concentration range titrating as 87 to 95 weight percent sulfuric acid/water mixtures, while sulfuric acid in the C5 alkylation reactor may be maintained at a concentration range titrating as 80 to 95 weight percent sulfuric acid/water mixtures.

The alkylation products recovered via flow line 16 may then be separated into gasoline range components and heavier alkylate products. Systems according to embodiments herein may include a deisobutanizer 22 for separating the hydrocarbon effluent 16 into an isobutane fraction 24, a n-butane fraction 26, and a C5+ fraction 28. The system may also include a deisopentanizer 30 for separating the C5+ fraction 28 into an isopentane fraction 32 and a C6+ fraction 34. A splitter 36 may also be provided for separating the C6+ fraction into a light alkylate overhead fraction 38 and a heavy alkylate bottoms fraction 40.

Flow systems are provided to enable the flexible production of jet fuel and gasoline according to embodiments herein. A flow system may be provided for recycling the isobutane fraction 24 to the alkylation reaction zone, via flow line 42, recovering the isobutane fraction as an isobutane product, via flow line 44, and both recycling a portion 42 of the isobutane fraction to the alkylation reaction zone and recovering a portion 44 of the isobutane fraction as an isobutane product. A flow system may also be provided for recycling the isopentane fraction 32 to the alkylation reaction zone, via flow line 46, recovering the isopentane fraction as an isopentane product 48, and both recycling a portion 46 of the isopentane fraction to the alkylation reaction zone and recovering a portion 48 of the isopentane fraction as an isobutane product. Further, a flow system may be provided for recycling the light alkylate fraction 38 to the alkylation reaction zone, via flow line 50, recovering the light alkylate as a light alkylate product 52, and both recycling a portion 50 of the light alkylate fraction to the alkylation reaction zone and recovering a portion 52 of the light alkylate fraction as a light alkylate product. The recycle of light alkylate, or a portion thereof, may introduce hexenes and/or isohexane to the reaction zone, which may react to produce higher molecular weight alkylate.

A control system (not shown) may also be provided, such as a digital control system or similar process operation and control software and hardware used to control or operate valving and other aspects of a plant. Control systems according to embodiments herein may be configured to adjust a flow rate of each of the crude olefins 12 (C4 olefins and C5 olefins), the recycle isobutane fraction 42, the isopentane recycle fraction 46, and the light alkylate recycle fraction 50 to the alkylation reaction zone 10 to selectively increase or decrease a ratio of gasoline to jet fuel range hydrocarbons produced in the alkylation reaction zone 10 and recovered in effluent 16.

In some embodiments, the control system is further configured to adjust a reaction temperature of the one or more reactors in the alkylation reaction zone to increase or decrease a ratio of gasoline to jet fuel range hydrocarbons produced in the alkylation reaction zone. The control system may be further configured to adjust a flow rate of fresh acid catalyst to the one or more reactors in the alkylation reaction zone to increase or decrease a ratio of gasoline to jet fuel range hydrocarbons produced in the alkylation reaction zone. Further still, the control system may additionally or alternatively be configured to adjust operating conditions in the one or more reactors in the alkylation reaction zone to increase or decrease a ratio of gasoline to jet fuel range hydrocarbons produced in the alkylation reaction zone, where the operating conditions may be selected from one or more of acid strength, temperature, space velocity, mixing intensity, recycle isobutane to olefin ratio and recycle isopentane to olefin ratio, for example.

The system may also include a flow line 54 for recovering the C5+ fraction as a gasoline product fraction. As described above, the system as illustrated in FIG. 3 may be used in processes to effectively and efficiently vary the ratio of gasoline to jet fuel produced via alkylation, as needed to meet market demand. The processes for flexible production of gasoline and jet fuel may include feeding isoparaffins 14 and olefins 12, including C4 and/or C5 olefins, to an alkylation reaction zone 10 including one or more reactors for reacting the C4-C5 olefins with the isoparaffins in the presence of an acid alkylation catalyst 20 to produce a hydrocarbon effluent 16 and a spent acid stream 18. The hydrocarbon effluent 16 may then be separated into an isobutane fraction 24, a n-butane fraction 26, and a C5+ fraction 28. The C5+ fraction 28 may be separated into an isopentane fraction 32 and a C6+ fraction 34. Further, the C6+ fraction 34 may be separated into a light alkylate overhead fraction 38 and a heavy alkylate bottoms fraction 40.

Processes herein may also include alternately (i) increasing a ratio of gasoline to jet fuel range hydrocarbons in the alkylate and (ii) decreasing a ratio of gasoline to jet fuel range hydrocarbons in the alkylate. The alternately increasing and decreasing may include, for example, adjusting a flow rate to the alkylation reaction zone of each of the crude olefins 12 (which may be separate C4 olefin and C5 olefin feeds), isobutane recycle fraction 42, isopentane recycle fraction 46, and light alkylate recycle fraction 50. The alternately increasing and decreasing, in some embodiments, may include adjusting a reaction temperature of one or more of the one or more reactors in the alkylation reaction zone to increase or decrease a ratio of gasoline to jet fuel range hydrocarbons produced in the alkylation reaction zone. The alternately increasing and decreasing may include, in some embodiments, adjusting a flow rate of fresh acid catalyst to the one or more reactors in the alkylation reaction zone to increase or decrease a ratio of gasoline to jet fuel range hydrocarbons produced in the alkylation reaction zone. Additionally, or alternatively, the alternately increasing and decreasing may include adjusting operating conditions in the one or more reactors in the alkylation reaction zone to increase or decrease a ratio of gasoline to jet fuel range hydrocarbons produced in the alkylation reaction zone, where the operating conditions are selected from one or more of acid strength, space velocity, mixing intensity, recycle isobutane to olefin ratio and recycle isopentane to olefin ratio.

In some embodiments, the alternately increasing comprises recovering the C5+ fraction, or a portion thereof, as a gasoline product fraction, such as via flow line 54. In embodiments where the totality of the C5+ fraction is recovered as a product, the depentanizer 30 and the splitter 36, and the associated flow streams, may be temporarily shut down. As it is desired to increase jet fuel production, such systems (30, 36, and associated flow streams) may be brought back online. In such embodiments, the control system may be further configured to shut down and start up the depentanizer and the splitter when increasing/maximizing the gasoline product fraction or decreasing/minimizing the gasoline product fraction, respectively In some embodiments, the olefin to isoparaffin mole ratio in the total reactor feed (crude olefin, isoparaffin, and recycle hydrocarbons) for each of the alkylation reaction zones may be in the range from about 1:1.5 to about 1:30, such as from about 1:5 to about 1:15. Lower olefin to isoparaffin ratios may also be used. The ratio of total recycle isoparaffin to olefins in the alkylation reactor(s) may be in the range of 1:1 to 20:1.

In maximizing gasoline production, the isobutane concentration in the total recycle isoparaffin stream may be in the range of 80-100%. Temperatures in the reactors may be in the range of −10° C. to 50° C., for example. In some embodiments, the alkylation of C4 olefins and/or C5 olefins may be in the range from about −7° C. to about 38° C.

In maximizing jet fuel production, the isobutane concentration in the total recycle isoparaffin stream may be in the range of 0-80%. The operating temperatures of the alkylation reactors may be the same or higher than when maximizing gasoline. Likewise, the acid strength may be the same or lower, and the space velocity may be the same or higher than when maximizing gasoline production.

Figure 4:
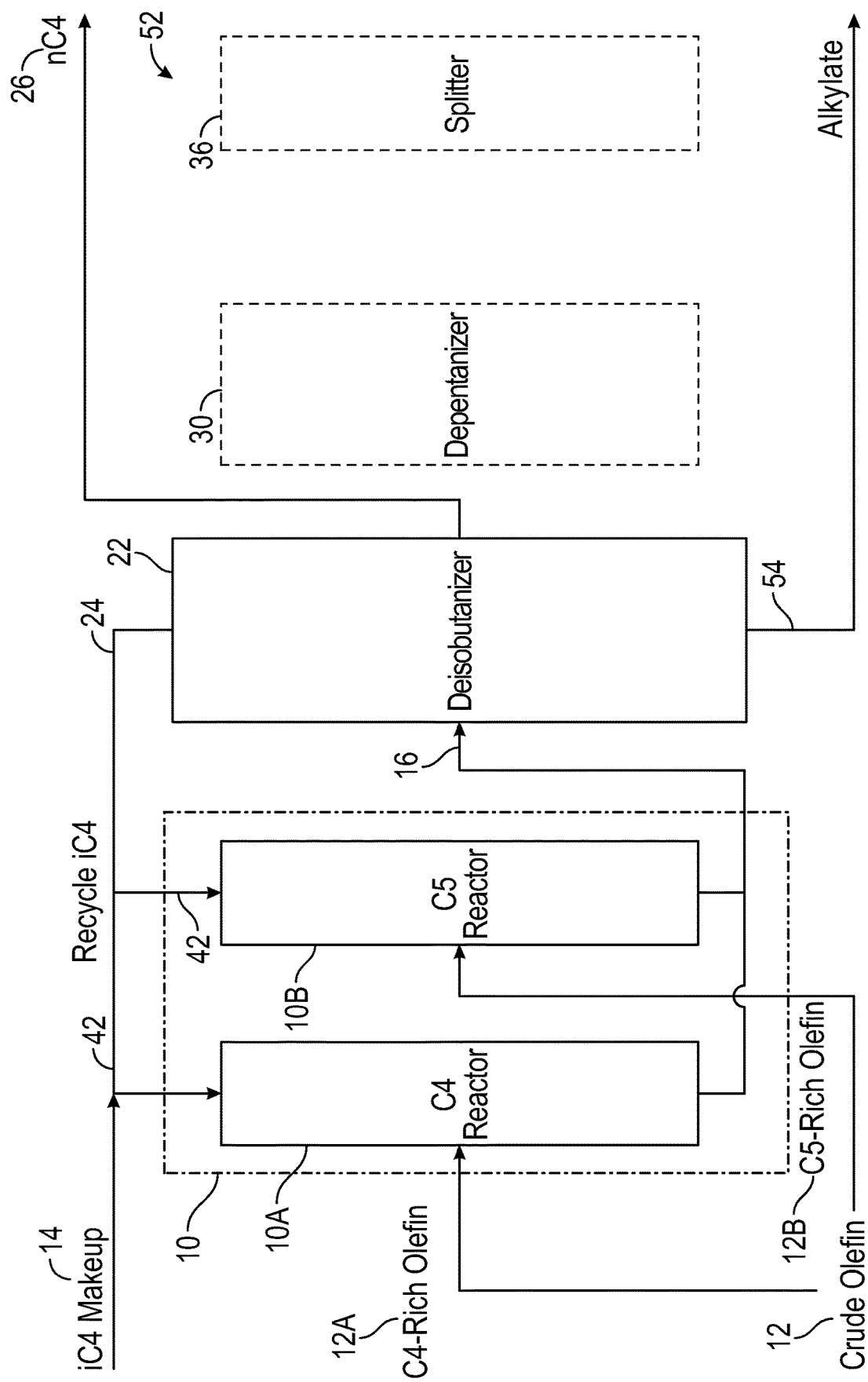
Figure 5:
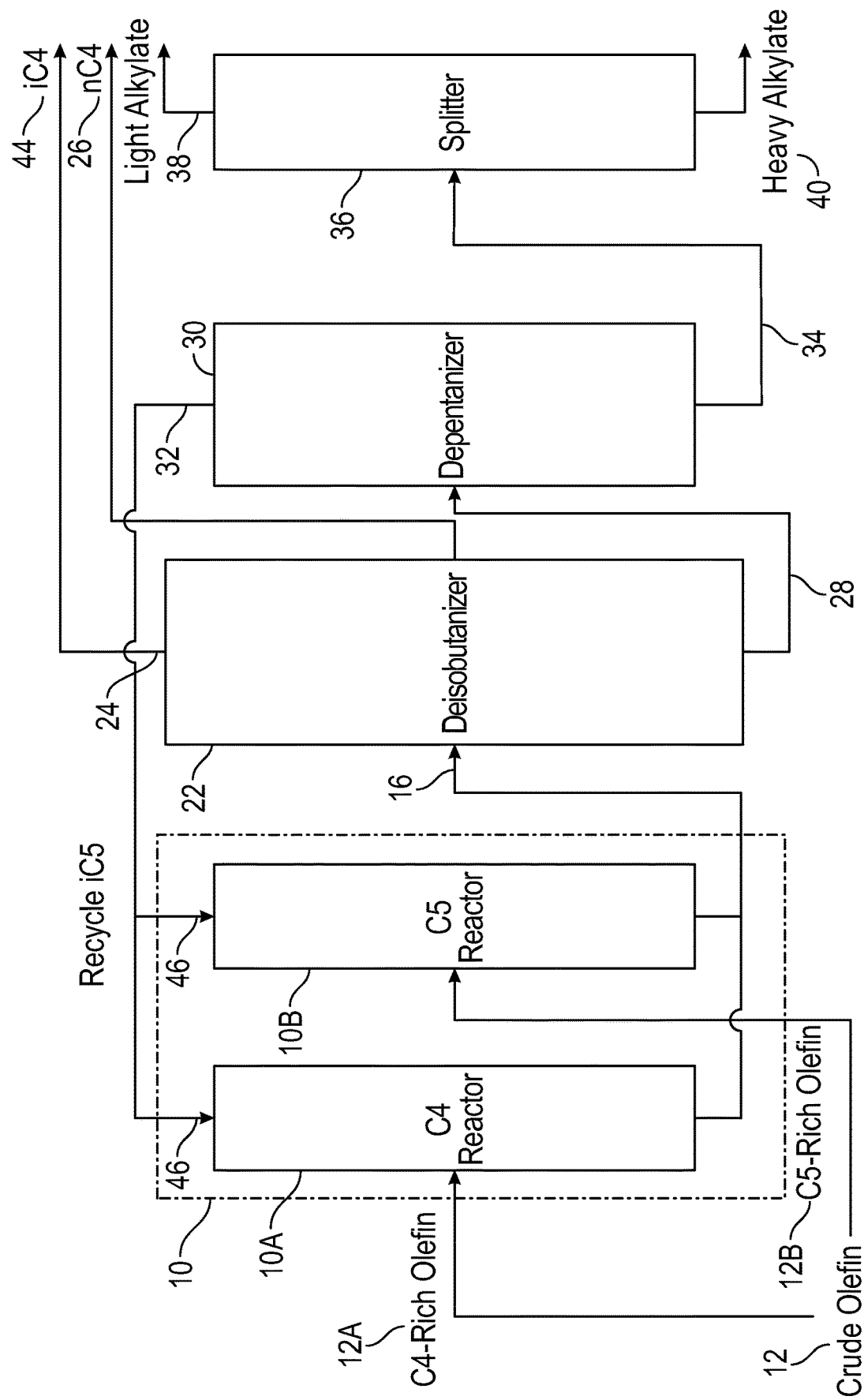
Figure 6:
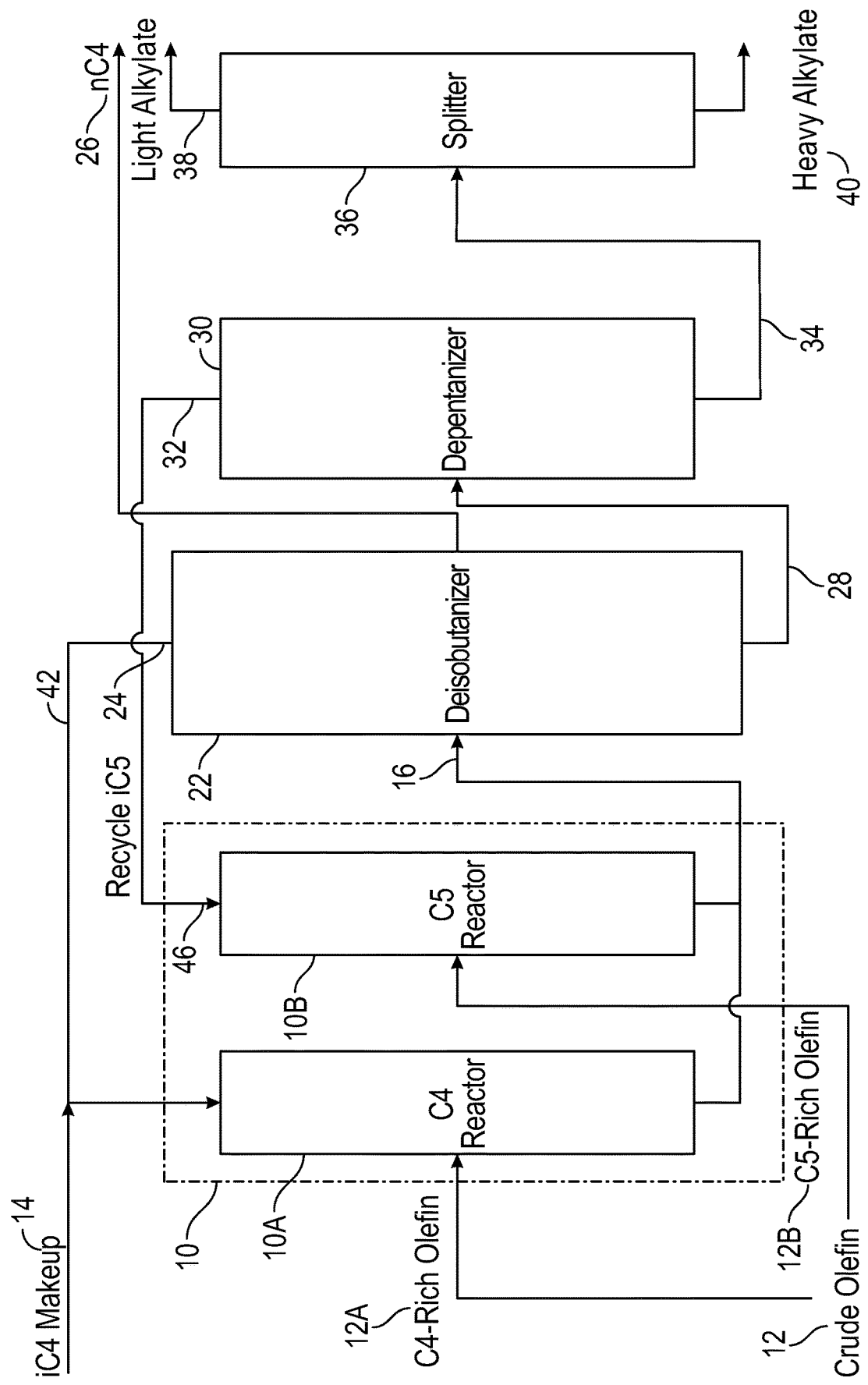

In some embodiments, such as illustrated collectively in FIGS. 4-6, the C4 rich olefin feed and the C5 rich olefin feed are processed in separate, dedicated reactors. The process scheme of FIGS. 4-6 is collective, where FIG. 4 illustrates the C4/C5 alkylation process scheme in maximizing gasoline mode, FIG. 5 illustrates the C4/C5 alkylation process scheme in maximizing jet fuel mode, and FIG. 6 illustrates the C4/C5 alkylation process scheme in coproduction mode. The reaction zone 10 may include a C4 alkylation reactor 10A and a C5 alkylation reactor 10B, and crude olefin feed 12 may include a crude C4 olefin feed 12A and a crude C5 olefin feed 12B FIGS. 4-6 illustrate the hydrocarbon flow streams and systems in operation during the respective mode, whereas the overall system may be similar to that as illustrated in FIG. 3, with certain equipment or flow lines off-line. Although the acid flows are not illustrated, these are also similar to shown and described with respect to FIG. 3.

Referring now to FIG. 4, a simplified flow diagram of C4/C5 alkylation process embodiments herein in a scheme maximizing gasoline production, where like numerals represent like parts. In the maximum-gasoline mode, as shown in FIG. 4, only isobutane 24/42 is recycled. The operating conditions in both reactors 10A/10B may target a lower space velocity, lower temperature, higher acid strength, and higher Isobutane/Olefin ratio compared to jet fuel or co-production modes. Depentanizer 30 and splitter 36 are off-line in the maximum gasoline mode.

Referring now to FIG. 5, a simplified flow diagram of C4/C5 alkylation process embodiments herein in a scheme maximizing jet fuel production, where like numerals represent like parts. In the maximum-jet fuel mode, as shown in FIG. 5, the isopentane recycle 32/46 should be maximized. Isobutane should be removed from the system as a net product 44. A certain isobutane recycle (42, not shown in FIG. 5) may be needed to control the concentration of heavies, in order to meet the end point (FBP) requirement. Regarding operating conditions, in overall, higher space velocity, higher temperature, lower acid strength and lower recycle I/O ratio is preferred for both reactors as compared to gasoline production mode.

Referring now to FIG. 6, a simplified flow diagram of C4/C5 alkylation process embodiments herein in a scheme coproducing gasoline and jet fuel, where like numerals represent like parts. In the co-production mode, as shown in FIG. 6, isobutane 42 is preferably recycled back to the C4 alkylation reactor, and isopentane 46 is preferably recycled back to C5 reactor, as C4 alkylation tends to produce alkylate with much higher octane compared to C5 alkylation. Reacting C4 olefin with isobutane, while reacting C5 olefin with isopentane may best monetarize their specific reaction chemistry. In addition, the C5 reactor is preferably operated at a much higher temperature and lower acid strength compared to the C4 reactor in co-production mode.

The flow systems associated with the fresh isoparaffin feeds 14, recycle isoparaffins 42/46/50, and crude olefins 10/10A/10B may provide for mixing of the respective fractions, feed of C4 olefins or isoparaffins to the C5 reactor, feed of C5 olefins or isoparaffins to the C4 reactor, or other combinations to provide further flexibility in the product make.

Embodiments of the C4/C5 alkylation processes described with respect to FIGS. 4-6 may include an acid strength in the C4 reactor in the range of 87-95% and an acid strength in the C5 reactor in the range of 80-95%. Isoparaffins may be recycled back to both the C4 and C5 reactors.

The ratio of total recycle isoparaffin to olefins in both reactors may be in the range of 1:1 to 20:1. In maximizing-gasoline mode, the isobutane concentration in total recycle isoparaffin back to two reactors are in the range of 80-100%. In maximizing-jet fuel mode, the isobutane concentration in total recycle isoparaffin back to two reactors are in the range of 0-80%. The operating temperatures in jet fuel mode may be the same or higher than during gasoline mode. Likewise, the acid strength may be the same or lower in jet fuel mode, and the space velocity may be the same or higher than in claim.

In co-production mode, the isobutane concentration in the total recycle isoparaffin back to C4 reactor may be in the range of 80-100%, and the isobutane concentration in total recycle isoparaffin back to C5 reactor may be in the range of 0-80%. The C4 reactor may have the same or higher acid strength than the C5 reactor, and the C4 reactor may have the same or lower temperature than the C5 reactor.

Figure 7:
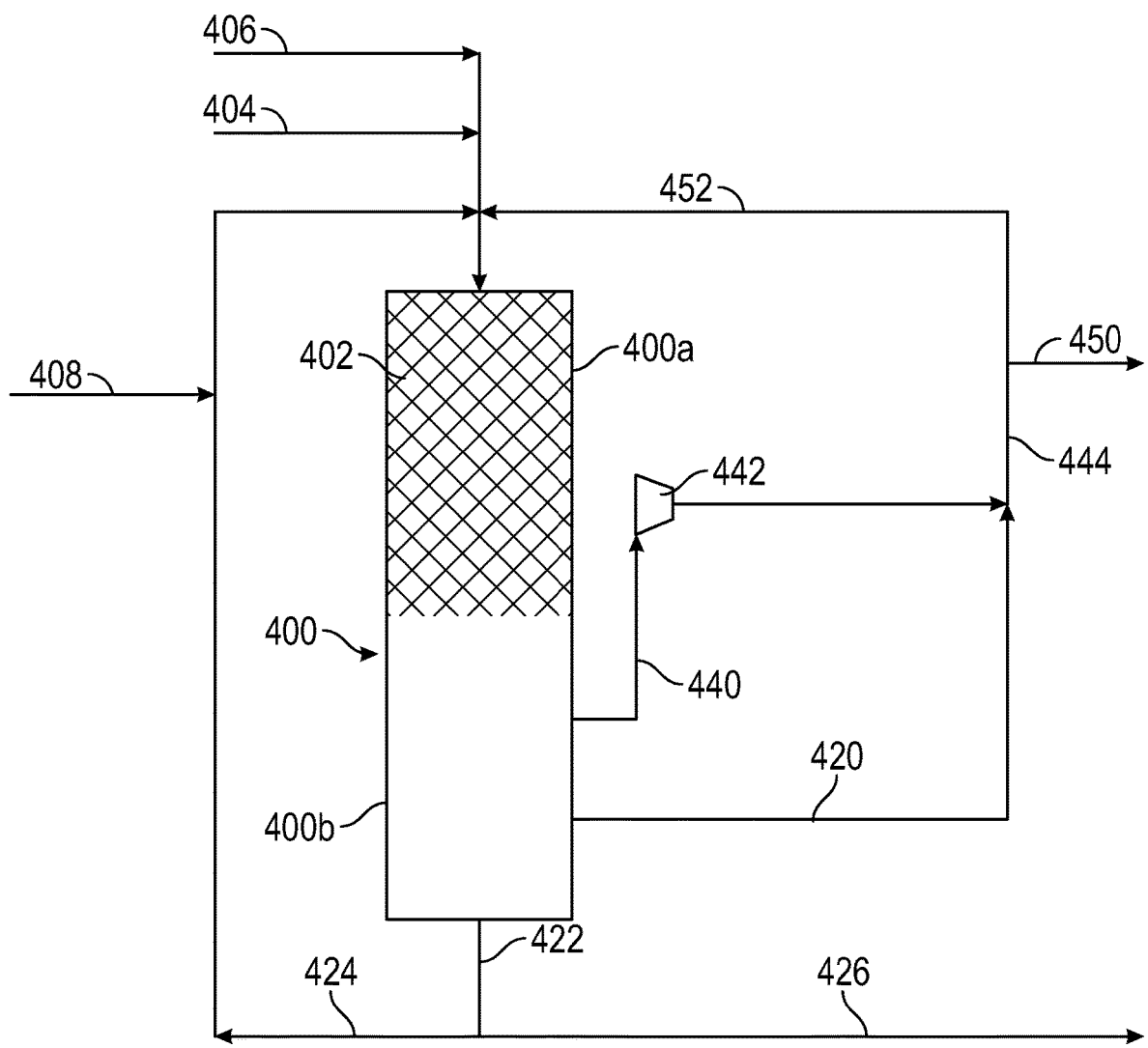
FIG. 7 illustrates an alkylation reaction system useful in the alkylation reaction zones according to embodiments herein.

Referring now to FIG. 7, a simplified process diagram of an alkylation zone according to one or more embodiments herein is illustrated. An alkylation zone may include a reaction zone and a separation zone. The alkylation zone 100, for example, may include an upper reaction section 100a and a bottom separation section 100b. Contact structures 102 may be positioned in upper section 100a to facilitate the intimate contact of the olefin 104, isoparaffin 106, and the sulfuric acid 108.

Conditions in the alkylation zone 100 may be maintained such that at least a portion or all of the olefin reacts with the isoparaffin to form alkylate, as mentioned above. The resulting reaction mixture may then be separated, for example, by decanting the reaction mixture in lower section 100b to recover a hydrocarbon fraction 120, including alkylate, unreacted isoparaffin, and any unreacted olefin, when present, and a spent or partially spent acid fraction 122.

If contact structures are used, they may be positioned in upper section 100a of the alkylation reactor 100 for contacting the sulfuric acid, isoparaffin and the olefin feed streams. In some embodiments, contact structures or dispersers used in embodiments described herein may include at least 50 percent void space; at least 60 percent void space in other embodiments; at least 70 percent void space in other embodiments; at least 80 percent void space in other embodiments; and up to 99 percent void space in yet other embodiments. For example, in some embodiments, a contact structure may include a multi-filament component and a structural element, such as a co-knit wire mesh, dispersers, or other suitable contact structures. For example, contact structures as described in U.S. Pat. No. 6,774,275, incorporated herein by reference, may be used.

In some embodiments, a pulse flow regime may also be used for the reaction zone of the alkylation reactors 100. The pulses may be characterized by large mass and heat transfer rates. Increased contact structure wetting and a continuous mixing between parallel flowing rivulets may diminish flow maldistribution. In addition, the formation of local hot spots may be reduced, leading to an intrinsically safer process. The pulses may continuously mobilize stagnant liquid holdup to the point where its stagnant nature disappears. Since stagnant holdup represents 10 to 30 percent of the total liquid holdup in trickle flow operations, the dynamic character of the pulse flow regime may enhance reactor performance, such as by improved radial mixing.

A portion or all of a partially spent acid fraction 122 recovered from an alkylation zone may be fed to another alkylation zone (not illustrated), as described above. In some embodiments, a portion 124 of the acid fraction 158 may also be recycled to the same alkylation reactor 100, such as to maintain a desired acid concentration in the first alkylation reactor 100. The remaining acid may be recovered as spent acid fraction 126, which may be forwarded to a different reactor or recovered for spent acid recovery.

Additionally, the heat of reaction may produce some vapors 140, which may be removed. If desired, these vapors may be condensed or compressed, such as by using a compressor 142, and combined with the recovered liquid hydrocarbon fraction 120 to form hydrocarbon fraction 144. In some embodiments, the recovered hydrocarbon fraction 144 may be split into a first portion 150 to be sent to a downstream alkylation zone or product recovery zone, and a second portion 152 may be recycled to the same alkylation reactor 100, such as to maintain a desired olefin feed concentration and/or for temperature control.

Examples

Figure 8:
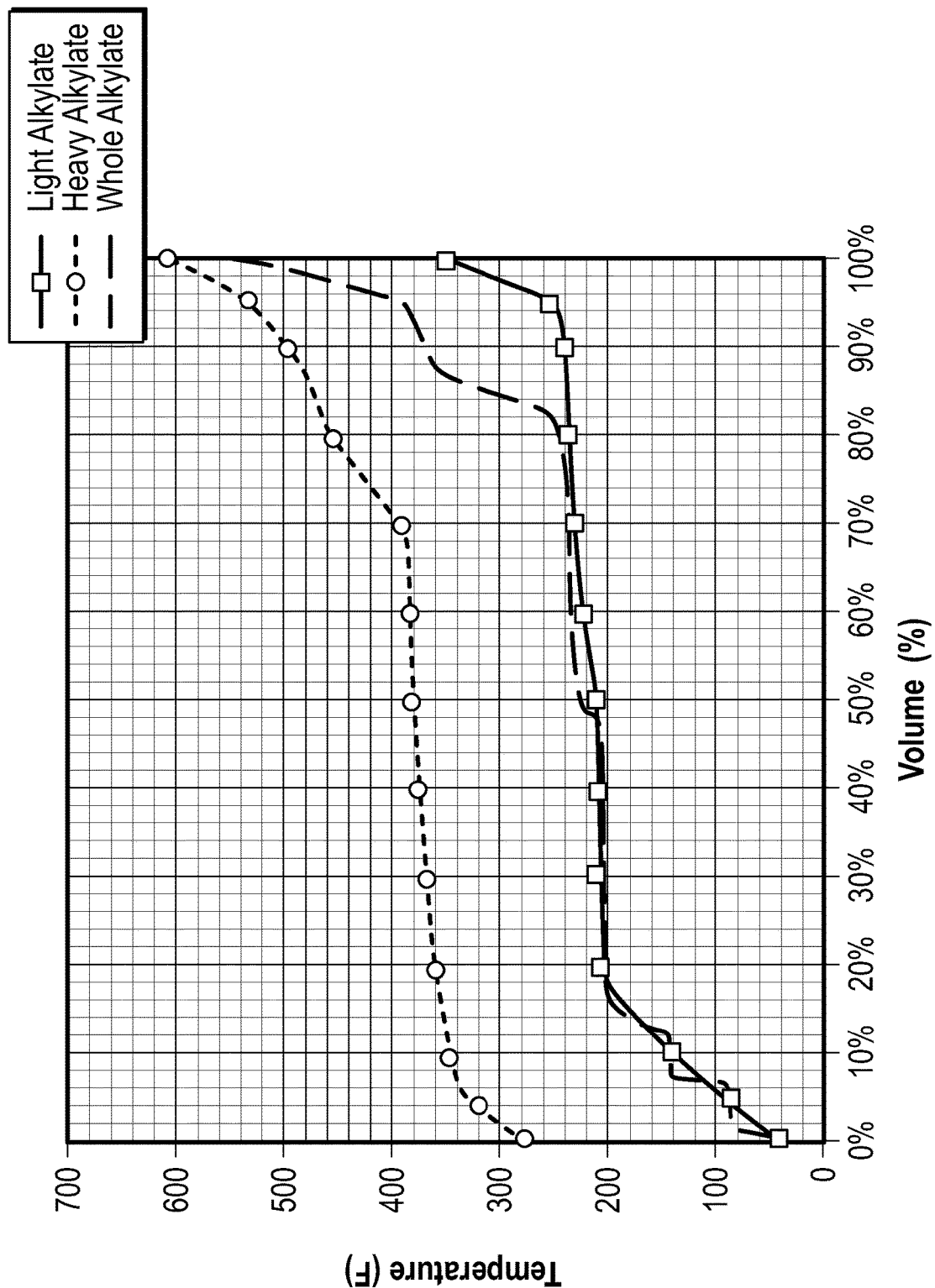
FIGS. 8 and 9 illustrate test results for processes producing jet fuel and gasoline according to embodiments herein.
Figure 9:
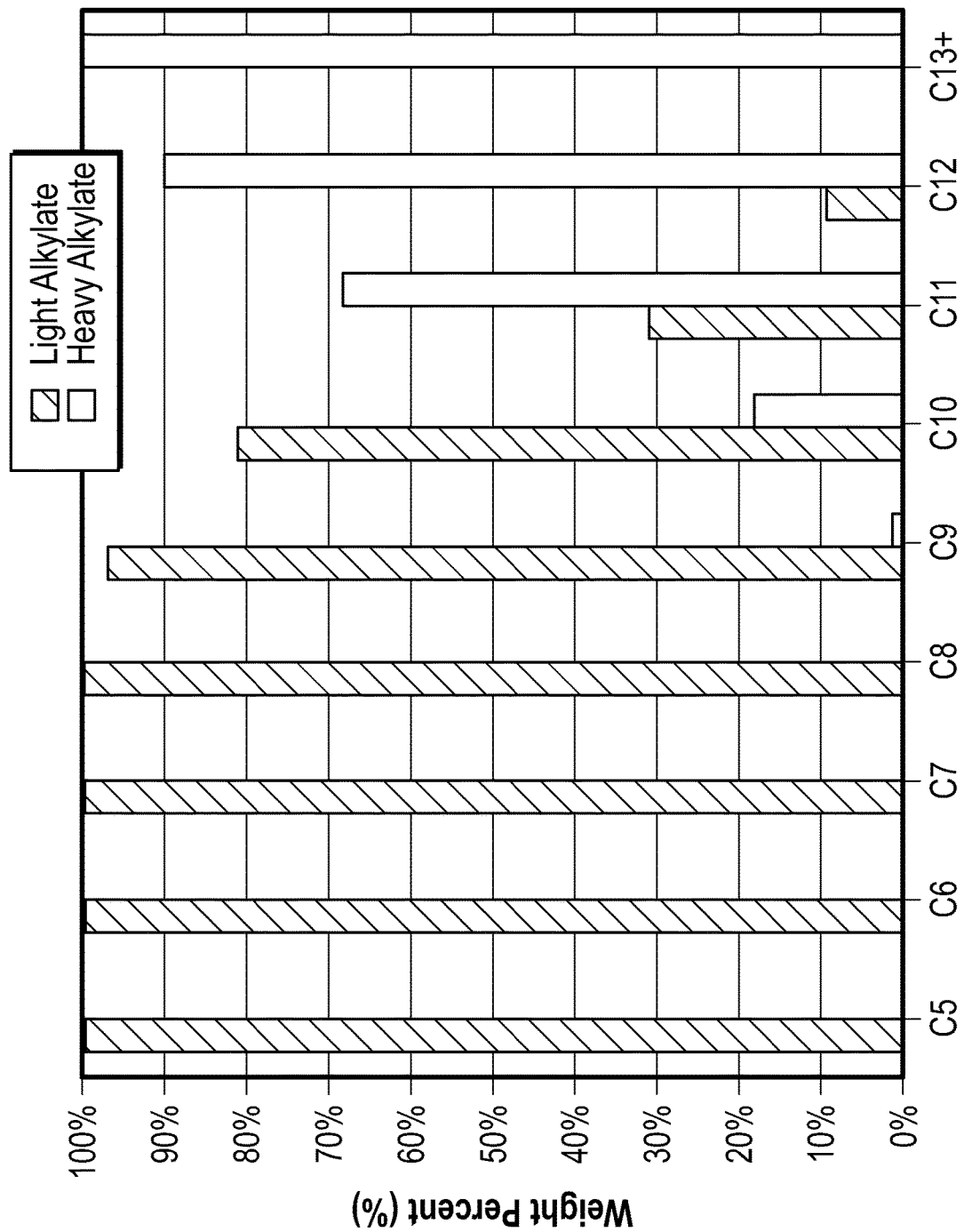

In a pilot plant test run, a FCC C4 cut and isobutane were used as a feedstock to a process similar to that as illustrated in FIG. 3. The operating conditions were adjusted to alter the product distribution. By carefully choosing the cut point, the whole alkylate was then distilled into light alkylate and heavy alkylate. As shown in FIG. 8, the heavy alkylate has a boiling range in the jet fuel range. The light alkylate can be used as a blending component for either aviation gasoline or motor gasoline. FIG. 9 gives the carbon number distribution of light alkylate and heavy alkylate. It is clear that, after the distillation, most of the C11+ product goes into the heavy alkylate.

In the test run, varied the operating conditions were used to obtain different jet fuel yield. With higher jet fuel yield, the alkylate quality (octane number) of light alkylate tends to get lower, and overall acid consumption tends to be higher. Thus, depending on the olefin types and price difference between gasoline and jet fuel, optimal operating condition exist to co-produce gasoline and jet fuel in order to maximize revenue or meet market demand.

As described above, embodiments herein provide systems and processes to flexibly produce gasoline and jet fuel. There is a growing interest in C5 alkylation, as it reduces the overall RVP, increase volume yield, and octane, compared to blending of the C5 olefins into the gasoline pool directly. Meanwhile, the operating acid strength for C5 alkylation is much lower, allowing acid cascade from the existing C4 alkylation reactor to the C5 reactor. Advantageously, embodiments herein provide process schemes to co-process C4 olefins and C5 olefins for varied targets: maximizing gasoline yield, maximizing jet fuel yield, or an optimal coproduction of both.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for flexible production of gasoline and jet fuel, including operating the process in a gasoline production mode, a jet fuel production mode, and a co-production mode, the process comprising:
    feeding isobutane and butenes to a C4 alkylation reactor for reacting the isobutane and butenes in the presence of sulfuric acid alkylation catalyst to produce a first alkylation effluent and a spent acid stream;
    feeding isopentane and pentenes to a C5 alkylation reactor for reacting the isopentane and the pentenes in the presence of sulfuric acid alkylation catalyst to produce a second alkylation effluent and a second spent acid stream; and
    separating the first and second alkylation effluents in a separation system comprising a debuanizer, a depentanizer, and an alkylate splitter, the separating comprising:
    (i) when operating in the gasoline production mode:
        feeding the first and second alkylation effluents to the debutanizer;
        separating the first and second alkylation effluents into an isobutane fraction, a n-butane fraction, and a C5+ fraction;
        recycling the isobutane fraction to both of the C4 alkylation reactor and the C5 alkylation reactor; and
        bypassing the depentanizer and the alkylate splitter and recovering the C5+ fraction as a gasoline product;
    (ii) when operating in the jet fuel production mode:
        separating the first and second alkylation effluents in the debutanizer to recover an isobutane fraction, a n-butane fraction, and a C5+ fraction;
        separating the C5+ fraction in the depentanizer to recover an isopentane fraction and a C6+ fraction;
        separating the C6+ fraction in the splitter into a light fraction and a heavy fraction; and
        feeding the isopentane fraction to both of the C4 and C5 alkylation reactors;
    (iii) when operating in the co-production mode:
        separating the first and second alkylation effluents in the debutanizer to recover an isobutane fraction, a n-butane fraction, and a C5+ fraction;
        separating the C5+ fraction in the depentanizer to recover an isopentane fraction and a C6+ fraction;
        separating the C6+ fraction in the splitter into a light fraction and a heavy fraction;
        feeding the isobutane fraction to the C4 alkylation reactor; and
        feeding the isopentane fraction to the C5 alkylation reactor.

2. The process of claim 1, further comprising:
    maintaining the sulfuric acid alkylation catalyst in the C4 alkylation reactor at a concentration range titrating as 87 to 95 wt % sulfuric acid/water mixtures, and
    maintaining the sulfuric acid alkylation catalyst in the C5 alkylation reactor at a concentration range titrating as 80 to 95 wt % sulfuric acid/water mixtures.

3. The process of claim 1, wherein operating in the jet fuel mode further comprises recycling the light fraction to the C4 and C5 alkylation reactors.

4. The process of claim 1, wherein operating in the jet fuel mode further comprises separating the light fraction to recover an isohexane-containing fraction and feeding the isohexane-containing fraction to one or both of the C4 alkylation reactor and the C5 alkylation reactor.

5. The process of claim 1, further comprising:
    operating the C4 and C5 alkylation reactors at a lower temperature during jet fuel mode than during gasoline production mode; and
    operating the C4 and C5 alkylation reactors at a lower acid strength during jet fuel mode than during gasoline production mode.

* * * * *